(12) United States Patent
Megens et al.

(10) Patent No.: US 11,872,075 B2
(45) Date of Patent: Jan. 16, 2024

(54) INTERVENTIONAL DEVICE POSITIONING RELATIVE TO AN ULTRASOUND IMAGE PLANE

(71) Applicant: KONINKLIJKE PHILIPS N.V., Eindhoven (NL)

(72) Inventors: Mischa Megens, Utrecht (NL); Hendrik Roelof Stapert, Eindhoven (NL); Mustafa Hakan Gokgurler, Helmond (NL); Stefan Van De Pas, Herten (NL); Jeroen Kortsmit, Son en Breugel (NL); Franciscus Hendrikus Van Heesch, Valkenswaard (NL); Harm Jan Willem Belt, Weert (NL); Ameet Kumar Jain, Boston, MA (US); Kunal Vaidya, Boston, MA (US); Francois Guy Gerard Marie Vignon, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 102 days.

(21) Appl. No.: 17/265,618

(22) PCT Filed: Aug. 7, 2019

(86) PCT No.: PCT/EP2019/071163
§ 371 (c)(1),
(2) Date: Feb. 3, 2021

(87) PCT Pub. No.: WO2020/030665
PCT Pub. Date: Feb. 13, 2020

(65) Prior Publication Data
US 2021/0321977 A1 Oct. 21, 2021

Related U.S. Application Data

(60) Provisional application No. 62/716,115, filed on Aug. 8, 2018.

(30) Foreign Application Priority Data

Oct. 5, 2018 (EP) ..................... 18198814

(51) Int. Cl.
*A61B 8/12* (2006.01)
*A61B 34/20* (2016.01)
(Continued)

(52) U.S. Cl.
CPC .............. *A61B 8/0841* (2013.01); *A61B 8/12* (2013.01); *A61B 8/5207* (2013.01); *A61B 2034/2063* (2016.02); *A61B 2090/3782* (2016.02)

(58) Field of Classification Search
CPC ....... A61B 8/0841; A61B 8/12; A61B 8/5207; A61B 2017/3413; A61B 90/37;
(Continued)

(56) References Cited

U.S. PATENT DOCUMENTS

| 4,249,539 A | 2/1981 | Vilkomerson |
| 6,556,957 B1 | 4/2003 | Daumer |

(Continued)

FOREIGN PATENT DOCUMENTS

| WO | 2011138698 A1 | 11/2011 |
| WO | 2015101949 A1 | 7/2015 |

(Continued)

OTHER PUBLICATIONS

International Search Report and Written Opinion of PCT/EP2019/071163, dated Dec. 2, 2019.

Primary Examiner — Colin T. Sakamoto
Assistant Examiner — Tommy T Ly

(57) ABSTRACT

System (10) for determining a position of an interventional device (11) respective an image plane (12) defined by an ultrasound imaging probe (13). The position is determined (Continued)

based on ultrasound signals transmitted between the ultrasound imaging probe (13) and an ultrasound transducer (15) attached to the interventional device (11). An image reconstruction unit (IRU) provides a reconstructed ultrasound image (RUI). A position determination unit (PDU) computes a position ($LAP_{TOFSmax, \theta IPA}$) of the ultrasound transducer (15) respective the image plane (12). The position determination unit (PDU) indicates the computed position ($LAP_{TOFSmax, \theta IPA}$) in the reconstructed ultrasound image (RUI). The position determination unit (PDU) suppresses the indication of the computed position ($LAP_{TOFSmax, \theta IPA}$) under specified conditions relating to the computed position ($LAP_{TOFSmax, \theta IPA}$) and the ultrasound signals.

20 Claims, 5 Drawing Sheets

(51) Int. Cl.
 *A61B 8/08* (2006.01)
 *A61B 90/00* (2016.01)
(58) Field of Classification Search
 CPC ...... A61B 2034/2063; A61B 2090/378; A61B 8/461; A61B 2090/3782; A61B 2090/3784; A61B 2090/3786; A61B 2090/3788; A61B 2034/107; A61B 8/15; A61B 8/4254; A61B 34/20; G01S 3/803
 See application file for complete search history.

(56) References Cited

U.S. PATENT DOCUMENTS

| | | |
|---|---|---|
| 2005/0038341 A1 | 2/2005 | Willis |
| 2007/0272019 A1* | 11/2007 | Agam .................. G01S 15/04 73/628 |
| 2010/0298704 A1 | 11/2010 | Pelissier |
| 2011/0213240 A1* | 9/2011 | Govari ................ A61B 8/0841 600/424 |
| 2013/0041252 A1 | 2/2013 | Vignon |
| 2016/0038119 A1* | 2/2016 | Desjardins ........... A61B 8/4444 600/424 |
| 2016/0157830 A1* | 6/2016 | Katsuyama ............. A61B 8/54 600/459 |
| 2016/0199025 A1* | 7/2016 | Takeda ................ A61B 8/0841 600/424 |
| 2016/0324501 A1* | 11/2016 | Vignon ................ A61B 8/4477 |
| 2017/0027605 A1 | 2/2017 | Erkamp |

FOREIGN PATENT DOCUMENTS

| | | | |
|---|---|---|---|
| WO | 2016009350 A1 | 1/2016 | |
| WO | WO-2017102369 A1 * | 6/2017 | ......... A61B 17/3403 |
| WO | WO-2017108490 A1 * | 6/2017 | ............ A61B 34/20 |
| WO | 2018060499 A1 | 4/2018 | |
| WO | 2018087111 A1 | 5/2018 | |
| WO | 2018108717 A1 | 6/2018 | |

* cited by examiner

INTERVENTIONAL DEVICE POSITIONING RELATIVE TO AN ULTRASOUND IMAGE PLANE

CROSS-REFERENCE TO PRIOR APPLICATIONS

This application is the U.S. National Phase application under 35 U.S.C. § 371 of International Application No. PCT/EP2019/071163, filed on Aug. 7, 2019, which claims the benefit of U.S. Provisional Patent Application Ser. No. 62/716,115, filed Aug. 8, 2018 and European Patent Application No. 18198814.8, filed on Oct. 5, 2018. These applications are hereby incorporated by reference herein.

FIELD OF THE INVENTION

The invention relates to determining a position of an interventional device respective an image plane of a beamforming ultrasound imaging probe.

BACKGROUND OF THE INVENTION

Interventional devices such as medical needles, catheters and surgical tools are often difficult to visualize in an ultrasound image due to the specular nature of their reflectivity, particularly at unfavorable incidence angles.

In this respect, document WO2018060499A1 describes a system for indicating a position of an interventional device feature of an interventional device respective an image plane defined by an ultrasound imaging probe of a beamforming ultrasound imaging system in which the position of the interventional device feature is determined based on ultrasound signals transmitted between the ultrasound imaging probe and an ultrasound transducer attached to the interventional device at a predetermined distance from the interventional device feature. An icon providing unit provides a first icon indicative of a circular zone with a radius corresponding to the predetermined distance. The first icon is displayed in a fused image that includes a reconstructed ultrasound image from the beamforming ultrasound imaging system.

Documents US 2016/0324501 A1, WO2011138698A1, WO2015101949A1 and WO2016009350A1 also describe systems for tracking an instrument in an ultrasound field with an ultrasound receiver that is mounted to the instrument. The position of the ultrasound receiver is subsequently displayed in an ultrasound image corresponding to the ultrasound field.

Despite these solutions there remains room for improved techniques for determining a position of an interventional device respective an ultrasound imaging plane.

SUMMARY OF THE INVENTION

In seeking to improve the positioning of an interventional device respective an image plane of a beamforming ultrasound imaging probe, a system is provided for determining a position of an interventional device respective an image plane defined by an ultrasound imaging probe of a beamforming ultrasound imaging system in which the position of the interventional device is determined based on ultrasound signals transmitted between the ultrasound imaging probe and an ultrasound transducer attached to the interventional device. The system includes an image reconstruction unit and a position determination unit. The image reconstruction unit provides a reconstructed ultrasound image corresponding to an image plane defined by the ultrasound imaging probe. The position determination unit computes a position of the ultrasound transducer respective the image plane based on a time of flight of a maximum detected intensity ultrasound signal transmitted between the ultrasound imaging probe and the ultrasound transducer; and indicates the computed position in the reconstructed ultrasound image. Moreover, the position determination unit suppresses the indication of the computed position if at least one of the following conditions are met:

- a rate of change of the computed position exceeds a first predetermined rate;
- an interference signal in the ultrasound signals exceeds a first predetermined value;
- the maximum detected intensity is less than a first predetermined threshold;
- a signal to noise ratio or a signal to interference ratio of the maximum detected intensity is less than a first predetermined level.

An issue that has been discovered by the inventors of the present invention is that the position determined by the position determination unit may be susceptible to errors. The likelihood of a potentially inaccurate position can be reliably determined by monitoring the aforementioned parameters. By suppressing the indication of the computed position under the aforementioned conditions, it is prevented that a potentially inaccurate position is indicated.

In accordance with one aspect the position determination unit continues suppressing the indication of the computed position until at least one of the following corresponding conditions have been satisfied for predetermined period:

- a rate of change of the computed position is less than a second predetermined rate;
- an interference signal in the ultrasound signals is less than a second predetermined value;
- the maximum detected intensity exceeds a second predetermined threshold;
- a signal to noise ratio or a signal to interference ratio of the maximum detected intensity exceeds a second predetermined level.

The second predetermined rate, value, threshold and level may be equal to or different from the corresponding first predetermined parameters. By continuing to suppress the indication of the computed position until the corresponding condition is met for a predetermined period, the reliability of the system is further improved because it is ensured that the computed position is not indicated again until the position has stabilized over time. The optional use of a different threshold adds hysteresis into the decision making. In so doing more reliable system is provided.

In accordance with one aspect the condition for suppressing indication of the computed position is based on an interference signal in the ultrasound signals exceeding a first predetermined value. The position determination unit measures the interference and/or noise signal in the ultrasound signals between consecutive imaging frame periods. Between consecutive frame periods there is a "quiet" period during which negligible ultrasound signals are expected to be transmitted by the ultrasound imaging probe and no reflected ultrasound signals are expected to be detected. Consequently this quiet period represents a time when only the interference and/or noise detected by the system can be reliably measured.

In accordance with one aspect the condition for suppressing indication of the computed position is based on an interference signal in the ultrasound signals exceeding a first predetermined value. The position determination unit measures the interference and/or noise signal in the ultrasound signals between consecutive image line periods. Image lines are typically transmitted consecutively, and include a transmit phase and a receive phase during which the ultrasound imaging probe transmits ultrasound signals and subsequently receives reflected ultrasound signals. Between the end of the receive phase of one imaging line and the transmit phase of the subsequent image line, there is a "quiet" period in which no reflections are expected. Consequently this quiet period represents a time when only the interference and/or noise detected by the system can be reliably measured.

In accordance with other aspects a method and corresponding computer program product that may be used in conjunction with the system are provided.

It is to be noted that the various aspects described in relation to the system may be combined to provide further advantageous effects. Moreover, aspects of the system may be used interchangeably with the method, and vice versa.

DETAILED DESCRIPTION OF THE INVENTION

In order to illustrate the principles of the present invention, various systems are described in which the position of an interventional device, exemplified by a medical needle, is indicated respective an image plane defined by a linear array of a 2D ultrasound imaging probe. Moreover, in some examples the position of a feature, such as the distal end, of the medical device is also tracked.

It is however to be appreciated that the invention also finds application with other interventional devices such as, and without limitation, a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool, a tissue sealing device, a tissue cutting device or an implantable device. The tracked feature of such interventional devices may exemplarily include a distal end of the interventional device, a biopsy sampling point of the interventional device, a cutting edge of the interventional device, an opening of a channel in the interventional device, a sensor (e.g. for sensing flow, pressure, temperature etc.) of the interventional device, a surgical tool (e.g. a scraper) integrated in the interventional device, a drug delivery point of the interventional device, or an energy delivery point of the interventional device.

Furthermore it is to be appreciated that the exemplified linear array of a 2D ultrasound imaging probe is only one example of an ultrasound transceiver array of a beamforming ultrasound imaging system in which the invention may be used. The invention also finds application in other types of beamforming ultrasound imaging systems whose associated ultrasound transceiver arrays exemplarily include a 2D array of a 3D imaging probe (or in bi-plane view), a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe.

Figure 1:
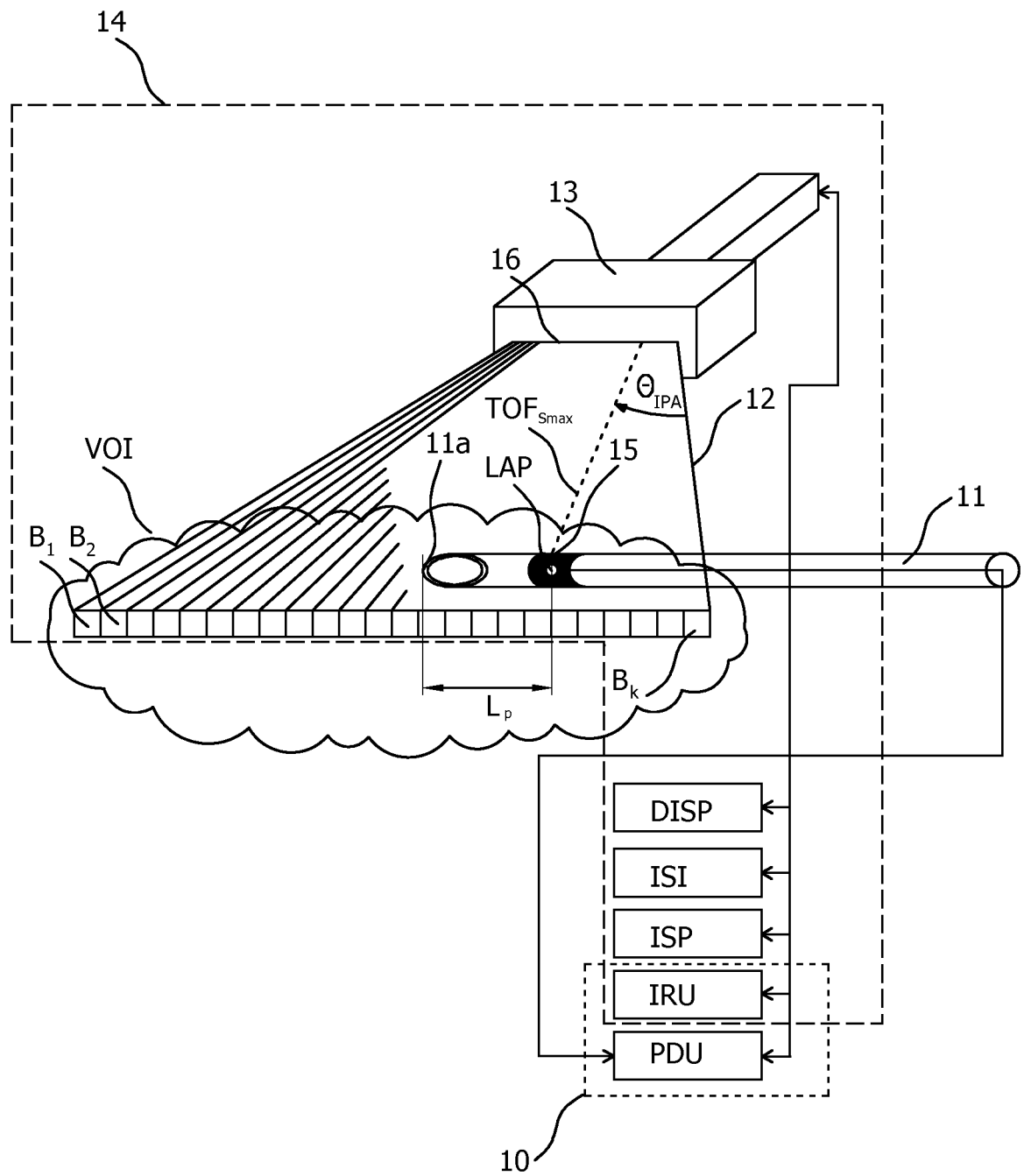
FIG. 1 illustrates a beamforming ultrasound imaging system 14 in combination with an in-plane interventional device 11 and an embodiment of the invention in the form of system 10.

FIG. 1 illustrates a beamforming ultrasound imaging system 14 in combination with an in-plane interventional device 11 and an embodiment of the invention in the form of system 10. In FIG. 1, beamforming ultrasound imaging system 14 includes a 2D ultrasound imaging probe 13 which is in communication with image reconstruction unit IRU, imaging system processor ISP, imaging system interface ISI and display DISP. The units IRU, ISP, ISI and DISP are conventionally located in a console that is in wired communication with 2D ultrasound imaging probe 13. It is also contemplated that wireless communication, for example using an optical, infrared, or an RF communication link, may replace the wired link. It is also contemplated that some of units IRU, ISP, ISI and DISP may instead be incorporated within 2D ultrasound imaging probe 13, as in for example the Philips Lumify ultrasound imaging system. In FIG. 1, 2D ultrasound imaging probe 13 includes linear ultrasound transceiver array 16 that transmits and receives ultrasound energy within an ultrasound field that intercepts volume of interest VOI. The ultrasound field is fan-shaped in FIG. 1 and includes multiple ultrasound beams $B_{1 \ldots k}$ that define image plane 12. Note that a fan-shaped beam is illustrated in FIG. 1 for the purposes of illustration only and that the invention is not limited to a particular shape of ultrasound field. Beamforming ultrasound imaging system 14 may also include electronic driver and receiver circuitry, not shown, that is configured to amplify and/or to adjust the phase of signals transmitted by or received by 2D ultrasound imaging probe 13 in order to generate and detect ultrasound signals in beams $B_{1 \ldots k}$. The electronic driver and receiver circuitry may thus be used to steer the emitted and/or received ultrasound beam direction.

In-use, beamforming ultrasound imaging system 14 is operated in the following way. An operator may plan an ultrasound procedure via imaging system interface ISI. Once an operating procedure is selected, imaging system interface ISI triggers imaging system processor ISP to execute application-specific programs that generate and interpret the signals transmitted by and detected by 2D ultrasound imaging probe 13. Beamforming ultrasound imaging system 14 may also include a memory, not shown, for storing such programs. The memory may for example store ultrasound beam control software that is configured to control the sequence of ultrasound signals transmitted by and/or received by ultrasound imaging probe 13. Image reconstruction unit IRU, which may alternatively form part of imaging system processor ISP, reconstructs data received from the ultrasound imaging probe 13 into an image corresponding to image plane 12 and which thus intercepts volume of interest VOI, and subsequently displays this image on display DISP. A planar section through volume of interest VOI is termed region of interest ROI herein. Reconstructed ultrasound image RUI may thus include region of interest ROI. The reconstructed image may for example be an ultrasound Brightness-mode "B-mode" image, otherwise known as a "2D mode" image, a "C-mode" image or a Doppler mode image, or indeed any ultrasound planar image.

Also shown in FIG. 1 is a medical needle 11 as an example of an interventional device, and an embodiment of the invention, system 10, that may be used to indicate a position of interventional device 11, i.e. the medical needle, respective image plane 12 of ultrasound imaging probe 13. This embodiment, system 10, includes image reconstruction unit IRU and position determination unit PDU. These units are in communication with one another as illustrated by the interconnecting arrows. It is also contemplated that one or more of units PDU, IRU may be incorporated within a memory or a processor of beamforming ultrasound imaging system 14, for example within a memory or a processor that also provides the functionality of unit ISP. Medical needle 11 that is tracked, includes ultrasound transducer 15 that may be positioned at predetermined distance $L_p$ from distal end 11a of interventional device 11.

In-use, a position of interventional device 11, or more specifically that of ultrasound transducer 15 attached thereto, is computed respective image plane 12 by position determination unit PDU based on ultrasound signals transmitted between ultrasound transceiver array 16 and ultrasound transducer 15.

In one configuration ultrasound transducer 15 is a detector that receives ultrasound signals corresponding to beams $B_{1 \ldots k}$. Position determination unit PDU identifies the lateral position LAP of ultrasound transducer 15 respective image plane 12 by correlating; i.e. comparing, the ultrasound signals emitted by ultrasound transceiver array 16 with the ultrasound signals detected by ultrasound transducer 15. More specifically this correlation determines the best fit position of ultrasound transducer 15 respective image plane 12 based on i) the intensities of the ultrasound signals corresponding to each beam $B_{1 \ldots k}$ that are detected by ultrasound transducer 15 and ii) based on the time delay, i.e. time of flight, between emission of each beam $B_{1 \ldots k}$ and its detection by ultrasound transducer 15. This may be illustrated as follows. When ultrasound transducer 15 is in the vicinity of image plane 12, ultrasound signals from the nearest of beams $B_{1 \ldots k}$ to the transducer will be detected with a relatively larger intensity whereas more distant beams will be detected with relatively smaller intensities. Typically the beam that is detected with the maximum detected intensity is identified as the one that is closest to ultrasound detector 15. In other words, the maximum detected intensity $I_{Smax}$ ultrasound signal identifies the in-plane angle $\Theta_{IPA}$ between ultrasound transceiver array 16 and ultrasound transducer 15. The time of flight, between the emission of this beam (from beams $B_{1 \ldots k}$) and its subsequent detection is indicative of the range between ultrasound transceiver array 16 and ultrasound transducer 15. Thus the time delay of the ultrasound signal in the beam that was detected with maximum detected intensity, $I_{Smax}$, i.e. $TOF_{Smax}$, is the ultrasound signal that is selected from the ultrasound signals of all beams. Since the time of flight is indicative of the range, in polar coordinates the lateral position of ultrasound transducer 15 respective image plane 12 may be represented by $LAP_{TOFSmax, \Theta_{IPA}}$. If desired, the range may be determined by multiplying the time delay by the speed of ultrasound propagation.

In another configuration ultrasound transducer 15 is an emitter that emits one or more ultrasound pulses. Such pulses may for example be emitted during tracking frames that are interleaved between the usual imaging frames of ultrasound imaging system 14. In such a tracking frame the ultrasound transceiver array 16 may be operated in a receive-only mode in which it listens for ultrasound signals originating from the vicinity of image plane 12. Ultrasound transceiver array 16 is thus configured as a one-way receive-only beamformer. Position determination unit PDU identifies from which beam of beams $B_{1 \ldots k}$ the pulse(s) originated based on the ultrasound signals emitted by ultrasound transducer 15 and those detected by ultrasound transceiver array 16. As in the configuration above, position determination unit PDU may use a correlation procedure that, based on the ultrasound signal detected with maximum intensity and its time of flight, identifies the closest beam and thus the point at which the ultrasound signal was emitted, i.e. its lateral position $LAP_{TOFSmax, \Theta_{IPA}}$ in the same manner. Thus, when ultrasound transducer 15 is an emitter, a correlation, i.e. comparison, procedure may again be used to determine its best-fit position respective image plane 12 for each tracking frame.

In another configuration ultrasound transducer 15 may be configured to act as both a receiver and an emitter, or include both a receiver and an emitter. In this configuration ultrasound transducer 15 may be triggered to emit one or more ultrasound pulses upon receipt of an ultrasound signal from ultrasound transceiver array 16; optionally following a delay that is equal to one or more frame periods of ultrasound imaging system 14. In this way the pulse(s) emitted by ultrasound transducer 15 during an imaging mode are received by ultrasound transceiver array 16 in the form of an echo in the reconstructed ultrasound at an in-plane angular position, i.e. in an image line, that corresponds to the triggering beam $B_{1 \ldots k}$. Ultrasound transducer 15 thus appears as a bright spot in the reconstructed image. Position determination unit PDU may subsequently identify this bright spot in the reconstructed image and thus again compute a lateral position $LAP_{TOFSmax, \Theta_{IPA}}$ of ultrasound transducer 15 respective image plane 12.

In yet another configuration, not illustrated, ultrasound imaging probe 13 may further include at least three ultrasound emitters that are attached to the ultrasound imaging probe 13. The at least three ultrasound emitters are in communication with position determination unit PDU. Moreover the position determination unit PDU is configured to compute a position of the ultrasound transducer 15 respective the image plane 12 based on ultrasound signals transmitted between the at least three ultrasound emitters attached to the ultrasound imaging probe 13, and the ultrasound transducer 15. In this configuration position determination unit PDU determines a range between each emitter and ultrasound transducer 15 based on the time of flight of ultrasound signals emitted by each emitter. The three dimensional position of ultrasound transducer 15 is subsequently determined using triangulation. This provides the position of ultrasound transducer 15 in three dimensions respective ultrasound imaging probe 13, or more specifically respective image plane 12 since the at least three emitters are attached to the ultrasound imaging probe 13. The three-dimensional position may subsequently be mapped to image plane 12 and thus again represented by $LAP_{TOFSmax, \Theta_{IPA}}$. Ultrasound emitters are preferred in this configuration because the supply of high power ultrasound signals to the emitters, necessary for accurate positioning over a large range, is simpler when the emitters are proximate ultrasound imaging probe 13 where a power source is readily available. This arrangement is thus preferred in contrast to locating a high power emitter on interventional device 11. In-use, the lateral position of interventional device 11, or more specifically that of ultrasound transducer 15 attached thereto, is thus again computed respective image plane 12 by position determination unit PDU based on ultrasound signals transmitted between the at least three emitters and ultrasound transducer 15.

Figure 3:
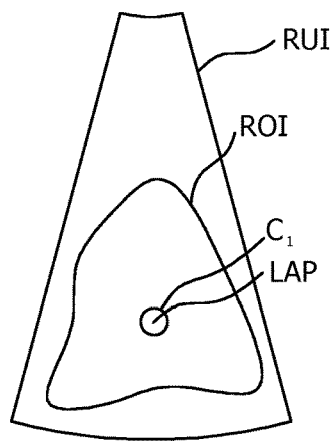
FIG. 3 illustrates a reconstructed ultrasound image RUI in which a computed position $LAP_{TOFSmax, \theta IPA}$ of the interventional device is indicated.

In summary, in this in-plane arrangement in which ultrasound transducer 15 is in the image plane, position determination unit PDU illustrated in FIG. 1 may be used in any of the above configurations to compute a lateral position of ultrasound transducer 15 respective image plane 12 based on ultrasound signals transmitted between ultrasound imaging probe 13 and ultrasound transducer 15. With reference to FIG. 3, which illustrates a reconstructed ultrasound image RUI in which a computed position $LAP_{TOFSmax, \theta IPA}$ of the interventional device is indicated, after computation of the position, computed position $LAP_{TOFSmax, \theta IPA}$ may be indicated in reconstructed ultrasound image RUI. Position LAP may for example be indicated as shown by the exemplary circle $C_1$, the center of which corresponds to computed position $LAP_{TOFSmax, \theta IPA}$. Alternative icons, shapes and indications may likewise be used. Whilst a circle is indicated in FIG. 3, other icons than a complete circle and which are likewise indicative of a circular zone may be used in the same manner, including e.g. a circular arrangement of dots or dashes, a circular arrangement of radially-directed lines or arrows, the tips of which indicate a circular zone, and so forth. In the exemplified circle in FIG. 3, the perimeter of the circle may indicate the limit of the uncertainty of position LAP, or a range of possible positions of e.g. a feature that is disposed on interventional device 11 at a predetermined distance from ultrasound transducer 15.

Figure 2:
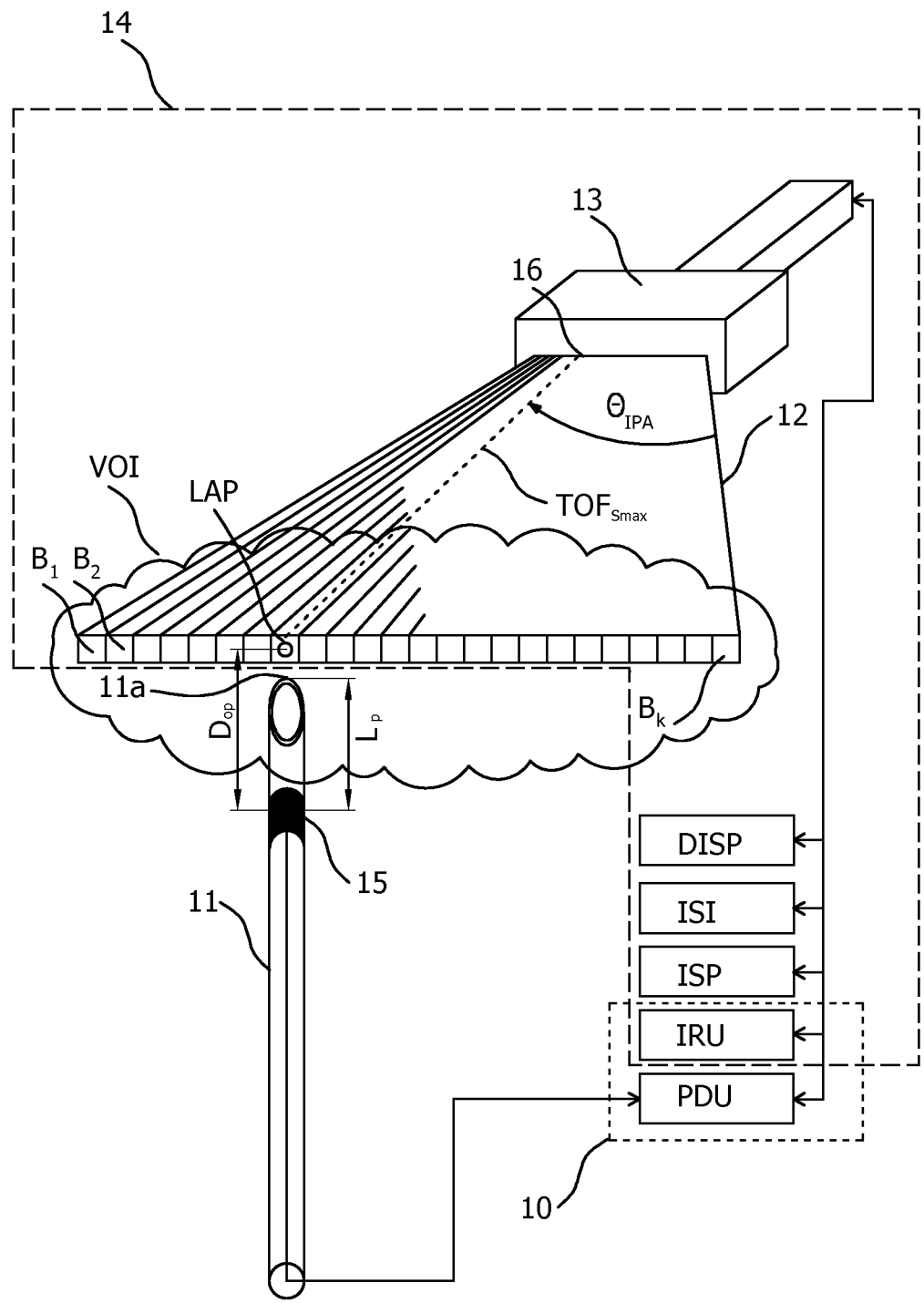
FIG. 2 illustrates a beamforming ultrasound imaging system 14 in combination with an interventional device 11 disposed at an out-of-plane distance $D_{op}$ and an embodiment of the invention in the form of system 10.

When ultrasound transducer 15 is disposed away from the image plane, i.e. out-of-plane, the same procedure may be used to determine a lateral position of ultrasound transducer 15, i.e. a position projected onto image plane 12. An additional procedure that uses the intensity, $I_{Smax}$, and the time of flight, $TOF_{Smax}$, of the ultrasound signal having the maximum detected intensity, may optionally be used to estimate a distance of ultrasound transducer 15 from image plane 12. In this respect, FIG. 2 illustrates a beamforming ultrasound imaging system 14 in combination with an interventional device 11 disposed at an out-of-plane distance $D_{op}$ and an embodiment of the invention in the form of system 10. Although beams $B_1 \ldots k$ of ultrasound imaging probe 13 are illustrated as being in plane 12, this plane has a finite thickness and a reduced ultrasound signal is typically detectable for small out-of-plane displacements. These signals are used in the present invention to estimate the out-of-plane distance $D_{op}$ of ultrasound transducer 15.

Various techniques may be used to determine the out-of-plane distance $D_{op}$. One technique involves using a transducer-specific three-dimensional map that associates a three dimensional position respective image plane 12 to an expected signal intensity. Having determined the lateral position $LAP_{TOFSmax, \theta IPA}$ of ultrasound transducer 15 respective image plane 12 as described above, the out of plane distance is determined by looking-up in the model the out of plane distance corresponding to the detected intensity, $I_{Smax}$, at that lateral position.

Figure 6:
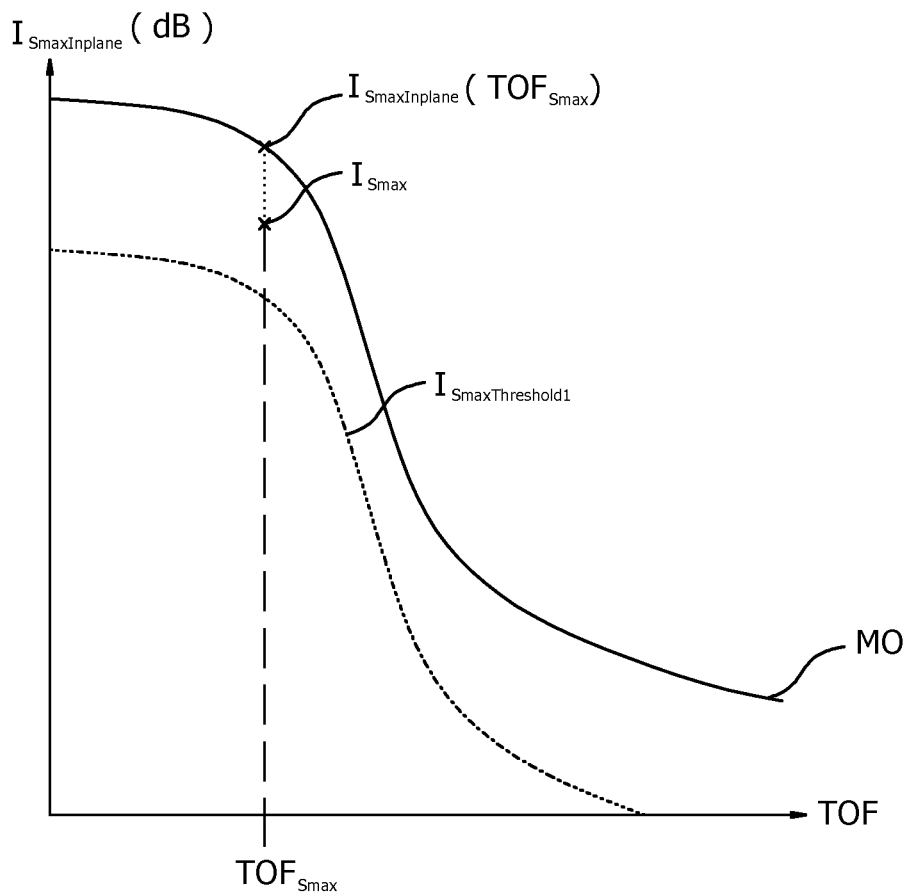
FIG. 6 illustrates a model MO describing an expected variation of in-plane maximum detected intensity, $I_{SmaxInplane}$ (dB) with time of flight, TOF.

Another technique is now described with reference to FIG. 6, which illustrates a model MO describing an expected variation of in-plane maximum detected intensity, $I_{SmaxInplane}$ (dB) with time of flight, TOF. With reference to FIG. 6, Model MO, indicated by the solid curve, illustrates that as the time of flight TOF, i.e. the depth into tissue increases, the in-plane maximum detected intensity, $I_{SmaxInplane}$, of detected ultrasound signals initially decreases slowly, then more rapidly, and then more slowly again. The shape of the model is affected by attenuation of ultrasound signals and may be determined from theoretical calculations or empirical measurements of the in-plane maximum intensity obtained in tissue or corresponding matter. Model MO depends only on time of flight and is invariant with in-plane angle $\theta_{IPA}$. It is noted that model MO does not model the maximum detected intensity, $I_{SmaxInplane}$ as a function of out-of-plane distance. Consequently model MO requires only a limited amount of, i.e. one-dimensional, calibration data. In contrast to the aforementioned three-dimensional model, in-use the out-of-plane distance may be determined with model MO with low latency due to the need to search in only one, i.e. time of flight, dimension. The modeled in-plane maximum detected intensity, $I_{SmaxInplane}$ has been found to reliably represent different beamforming ultrasound imaging probes of the same type, which means that the same model may be used for beamforming ultrasound imaging probes of the same type.

With reference to FIG. 2 and FIG. 3, in-use, computing out-of-plane distance $D_{op}$ comprises comparing the maximum detected intensity $I_{Smax}$ with model MO. The out-of-plane distance $D_{op}$ may subsequently be indicated in reconstructed ultrasound image RUT. The out-of-plane distance may be indicated numerically for example, or as a size, or a color of an icon that varies accordance with $D_{op}$. With reference to FIG. 3, in one implementation the out-of-plane distance $D_{op}$ may be indicated by means of varying the radius of circle $C_1$ in FIG. 3 in accordance with out-of-plane distance $D_{op}$. Comparing the maximum detected intensity $I_{Smax}$ with model MO may for instance involve determining a difference or ratio between detected intensity $I_{Smax}$ and the in-plane maximum detected intensity, $I_{SmaxInplane}$ at the time of flight $TOF_{Smax}$ corresponding to the computed lateral position $LAP_{TOFSmax}$. In one exemplary implementation the maximum detected intensity $I_{Smax}$ at the computed lateral position $LAP_{TOFSmax, \theta IPA}$ of the ultrasound transducer may thus be scaled to the in-plane maximum detected intensity $I_{SmaxInplane}$, at the time of flight $TOF_{Smax}$ corresponding to the computed lateral position $LAP_{TOFSmax, \theta IPA}$. A qualitative indication of the out-of-plane distance may subsequently be indicated in reconstructed ultrasound image RUI. For example, an icon may be displayed that has a size that varies in accordance with:

$$Size = k_1 + k_2 \cdot \left(1 - \frac{I_{Smax}}{I_{SmaxInplane}}\right) \quad \text{Equation 1}$$

and wherein $k_1$ and $k_2$ are constants and $k_1$ may include zero.

In another exemplary implementation, with reference to FIG. 3, the color of an icon may be configured to change based on the value of the maximum detected intensity $I_{Smax}$ in relation to $I_{SmaxInplane}$, at the time of flight $TOF_{Smax}$.

An issue that has been discovered by the inventors of the present invention is however that the so-determined position may be susceptible to errors. The determined position may for example be influenced by the presence of high levels of noise or interference. The determined position may likewise be influenced when the maximum detected intensity $I_{Smax}$ or its signal to noise ratio or its signal to interference ratio is low. Another indicator of the possibility of an incorrectly determined position is a high rate of change of the determined position. In order to mitigate such errors, in the present invention position determination unit PDU suppresses the indication of the computed position $LAP_{TOFSmax, \theta_{IPA}}$ if at least one of the following conditions are met:

- a rate of movement of the computed position $LAP_{TOFSmax, \theta_{IPA}}$ exceeds a first predetermined rate $R_{Max1}$;
- an interference signal in the ultrasound signals exceeds a first predetermined value $Int_{Threshold1}$;
- the maximum detected intensity $I_{Smax}$ is less than a first predetermined threshold $I_{SmaxThreshold1}$;
- a signal to noise ratio or a signal to interference ratio of the maximum detected intensity $I_{Smax}$ exceeds a first predetermined level $SNR_{ISmaxThreshold1}$.

Thus, with reference to exemplary FIG. 3, if one of the aforementioned conditions are met, position determination unit PDU may cease to display circle $C_1$.

In summary, and with reference to FIG. 1, FIG. 2, FIG. 3 and FIG. 6, a system 10 for determining a position of an interventional device 11 respective an image plane 12 defined by an ultrasound imaging probe 13 of a beamforming ultrasound imaging system 14 in which the position of the interventional device 11 is determined based on ultrasound signals transmitted between the ultrasound imaging probe 13 and an ultrasound transducer 15 attached to the interventional device 11, includes:

- image reconstruction unit IRU that provides reconstructed ultrasound image RUI corresponding to image plane 12 defined by ultrasound imaging probe 13; and
- position determination unit PDU that:
  - computes a position $LAP_{TOFSmax, \theta_{IPA}}$ of ultrasound transducer 15 respective image plane 12 based on a time of flight $TOF_{Smax}$ of a maximum detected intensity $I_{Smax}$ ultrasound signal transmitted between ultrasound imaging probe 13 and ultrasound transducer 15;
  - indicates the computed position $LAP_{TOFSmax, \theta_{IPA}}$ in the reconstructed ultrasound image RUI; and
  - suppresses the indication of the computed position $LAP_{TOFSmax, \theta_{IPA}}$ if at least one of the following conditions are met:
    - a rate of change of the computed position $LAP_{TOFSmax, \theta_{IPA}}$ exceeds a first predetermined rate $R_{Max1}$;
    - an interference signal in the ultrasound signals exceeds a first predetermined value $Int_{Threshold1}$;
    - the maximum detected intensity $I_{Smax}$ is less than a first predetermined threshold $I_{SmaxThreshold1}$;
    - a signal to noise ratio or a signal to interference ratio of the maximum detected intensity $I_{Smax}$ is less than a first predetermined level $SNR_{ISmaxThreshold1}$.

By so suppressing the indication of the computed position, it is prevented that a potentially inaccurate position is indicated.

The aforementioned conditions, i.e. the rate of change of the computed position, the interference signal in the ultrasound signals, the maximum detected intensity $I_{Smax}$, the signal to noise ratio or the signal to interference ratio of the maximum detected intensity $I_{Smax}$ may be measured by hardware or a software-controlled processor or a combination of hardware and a software-controlled processor. The position determination unit that decides and implements the result of testing the condition is preferably implemented by a software-controlled processor.

In respect of determining the rate of change of the computed position $LAP_{TOFSmax, \theta_{IPA}}$, position determination unit PDU which calculates position $LAP_{TOFSmax, \theta_{IPA}}$ may determine, in a suitable coordinate space, the rate of change of the position. The rate of change may for instance include an angular rate of change of in-plane angle $\theta_{IPA}$ and/or a rate of change of time of flight of the maximum detected ultrasound signal $TOF_{Smax}$. Alternatively the polar coordinates of the computed position may be converted into Cartesian coordinate space in order to determine the rate of change. First predetermined rate $R_{Max1}$ may be set based on the likely rate that a user might be expected to move an interventional device within image plane 12. By way of an example, it may be considered unlikely that an operator would move interventional device 11 by e.g. 45 degrees at a time of flight corresponding to 10 centimeters within one image frame at say 100 frames per second. Such a threshold may be used to set first predetermined rate $R_{Max1}$. When position determination unit indicates a rate of change of position that exceeds this rate, the indication of the position, e.g. the provision of circle $C_1$ in reconstructed ultrasound image RUI in FIG. 3, may be inhibited.

In respect of the interference signal in the ultrasound signals, the measurement technique depends on whether ultrasound transducer 15 is a transmitter of a detector. When ultrasound transducer 15 is a detector an electrical circuit may for example be used to determine the root mean square, rms, value of the interference and/or noise, in the electrical signals generated by the detector, or alternatively an analogue to digital converter may be used to sample these electrical signals and thus determine this value. Various hardware or software filters may be used to measure the noise and/or interference within a predetermined bandwidth, and/or to separate the noise and/or interference from concurrent ultrasound signals. When ultrasound transducer 15 is a transmitter and it is desired to determine interference signals in the detected ultrasound signals, this may be carried out by analyzing the signals detected by ultrasound imaging probe 13. Processor-implemented position determination unit PDU may determine the noise and/or interference from the digitized signals detected by ultrasound imaging probe 13 using equivalent software methods. Predetermined value $Int_{Threshold1}$ may be set e.g. based on typical measured or expected signal levels.

The value of the maximum detected intensity $I_{Smax}$ ultrasound signal transmitted between ultrasound imaging probe 13 and ultrasound transducer 15 is inherently available within the processor that provides position determination unit PDU since this value is used in computing position $LAP_{TOFSmax, \theta_{IPA}}$. Thus it becomes straightforward to compare the value $I_{Smax}$ with a first predetermined threshold $I_{SmaxThreshold1}$. First predetermined threshold $I_{SmaxThreshold1}$ may be set e.g. based on typical measured or expected signal levels.

The signal to noise ratio or the signal to interference ratio of the maximum detected intensity $I_{Smax}$ and its corresponding first predetermined level $SNR_{ISmaxThreshold1}$ may be determined and set using a combination of the aforementioned techniques described in relation to maximum detected intensity $I_{Smax}$ and the noise and/or interference signal in the detected ultrasound signals.

In some exemplary implementations position determination unit PDU may continue suppressing the indication of the computed position $LAP_{TOFSmax, \theta IPA}$ until at least one of the following corresponding conditions have been satisfied for a predetermined period:
- a rate of change of the computed position $LAP_{TOFSmax, \theta IPA}$ is less than a second predetermined rate $R_{Max2}$;
- an interference signal in the ultrasound signals is less than a second predetermined value $Int_{Threshold2}$;
- the maximum detected intensity $I_{Smax}$ exceeds a second predetermined threshold $I_{SmaxThreshold2}$;
- a signal to noise ratio or a signal to interference ratio of the maximum detected intensity $I_{Smax}$ exceeds a second predetermined level $SNR_{ISmaxThreshold2}$.

By continuing to suppress the indication of the computed position until the corresponding condition is met for a predetermined period, the reliability of the system is further improved because it is ensured that the computed position is not indicated again until the position has stabilized over time.

The predetermined period may for instance be measured in seconds or fractions of a second, or in an integer number of frames or image lines. Synchronization to the frame rate by means of the latter has the advantage of less complex implementation.

Moreover, whilst the corresponding rates, values, thresholds and levels that continue suppression of the indication of the position may differ from those triggering the suppression, in some implementations the first predetermined rate $R_{Max1}$ is equal to the second predetermined rate $R_{Max2}$; and in some implementations the first predetermined value $Int_{Threshold1}$ is equal to the second predetermined value $Int_{Threshold2}$; and in some implementations the first predetermined threshold $I_{SmaxThreshold1}$ is equal to the second predetermined threshold $I_{SmaxThreshold2}$; and in some implementations the first predetermined level $SNR_{ISmaxThreshold1}$ is equal to the second predetermined level $SNR_{ISmaxThreshold2}$. The use of the same corresponding rates, values, thresholds and levels facilitates a less complex implementation. The use of a different threshold adds hysteresis into the decision making. In so doing more reliable system is provided.

With reference to FIG. 4, which illustrates a succession of periodic updates, RUI', RUI" to reconstructed ultrasound image RUI, in some exemplary implementations position determination unit PDU is configured to suppress the indication of the computed position $LAP_{TOFSmax, \theta IPA}$ based on an interference signal in the ultrasound signals exceeding a first predetermined value $Int_{Threshold1}$. The magnitude of the interference signal may be determined as described above. Moreover, in such implementations image reconstruction unit IRU is configured to periodically update the reconstructed ultrasound image RUI; the ultrasound signals corresponding to each reconstructed ultrasound image RUI being transmitted and detected by the ultrasound imaging probe 13 during a corresponding imaging frame period $T_f$. Position determination unit PDU is configured to determine the interference signal in the ultrasound signals between consecutive imaging frame periods.

Figure 4A:
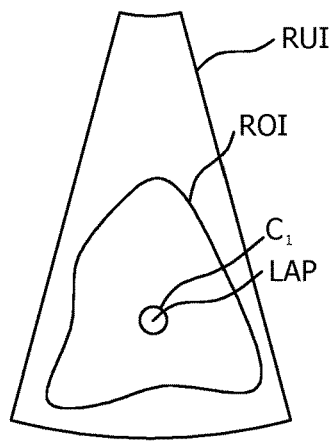
FIG. 4 illustrates a succession of periodic updates, RUI', RUI" to reconstructed ultrasound image RUI.
Figure 4B:
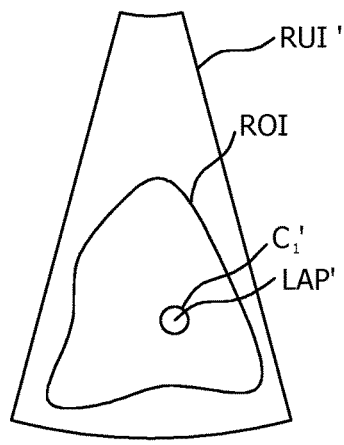
Figure 4C:
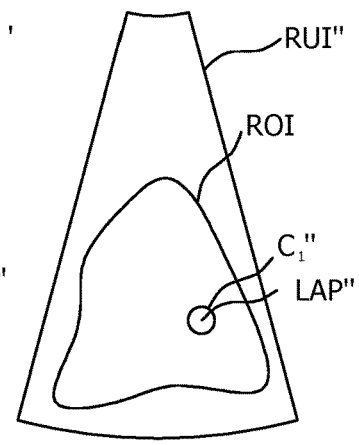
Figure 4D:
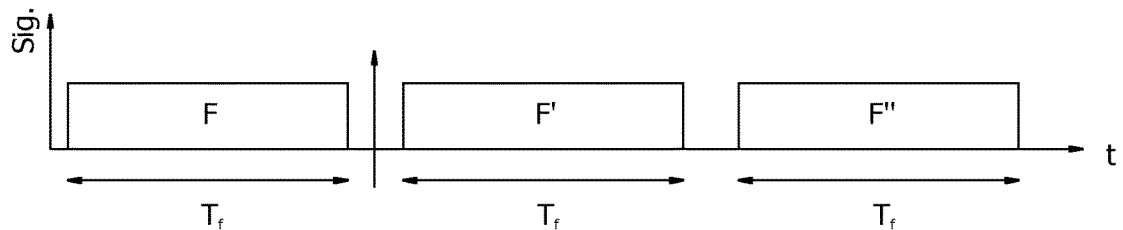

Throughout FIGS. 4B and 4C, updated reconstructed ultrasound images RUI' and RUI" indicate the progression of position-indicating circle $C_1$ horizontally and to the right of the figures. FIG. 4D indicates the corresponding imaging signals from beamforming ultrasound imaging probe 12, which are transmitted and detected within consecutive frames F, F' and F", each having a period $T_f$. Between consecutive frame periods there is a "quiet" period indicated by the vertical arrow in FIG. 4D during which negligible ultrasound signals are transmitted by the ultrasound imaging probe and no reflected ultrasound signals are expected to be detected. Consequently this quiet period represents a time when only the interference and/or noise detected by the system can be reliably measured. The interference and/or noise may exemplarily be measured between every frame, or between consecutive frames every N frames where N is an integer, or between consecutive frames after a random number of frames.

Figure 5A:
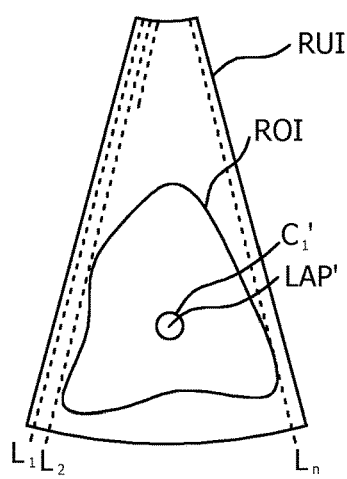
FIG. 5 illustrates a reconstructed ultrasound image RUI that includes multiple image lines $L_{1 \ldots n}$, each line corresponding to a time of flight or depth dimension in the ultrasound image.

With reference to FIG. 5, which illustrates a reconstructed ultrasound image RUI that includes multiple image lines $L_{1 \ldots n}$, each line corresponding to a time of flight or depth dimension in the ultrasound image, in some exemplary implementations position determination unit PDU is configured to suppress the indication of the computed position $LAP_{TOFSmax, \theta IPA}$ based on an interference signal in the ultrasound signals exceeding a first predetermined value $Int_{Threshold1}$. In such implementations reconstructed ultrasound image RUI comprises a plurality of image lines $L_{1 \ldots n}$, each line corresponding to a depth dimension in the ultrasound image; and wherein the ultrasound signals corresponding to each line of the reconstructed ultrasound image RUI are transmitted and detected by the ultrasound imaging probe 13 during a corresponding image line period $T_1$. Position determination unit PDU is configured to determine the interference signal in the ultrasound signals between consecutive image line periods.

Figure 5B:
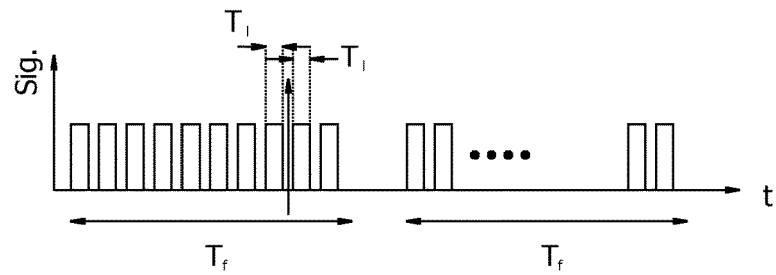

Ultrasound signals corresponding to image lines are typically transmitted in the consecutive manner illustrated in FIG. 5, and include, within image line period $T_1$, a transmit phase and a receive phase during which the ultrasound imaging probe transmits ultrasound signals and subsequently receives reflected ultrasound signals. Between the end of the receive phase of one imaging line and the transmit phase of the subsequent image line, there is a "quiet" period indicated by the vertical arrow in FIG. 5B and in which no reflections are expected. Consequently this quiet period represents a time when only the interference and/or noise detected by the system can be reliably measured. The interference and/or noise may exemplarily be measured between every line, or between consecutive lines after every M lines where M is an integer, or between consecutive lines after a random number of lines, or between the same two lines in consecutive or every N image frames.

With reference to FIG. 6, which illustrates a model MO describing an expected variation of in-plane maximum detected intensity, $I_{SmaxInplane}$ (dB) with time of flight, TOF, in some exemplary implementations, indicating the computed position $LAP_{TOFSmax, \theta IPA}$ in the reconstructed ultrasound image RUI may also include:
- computing an out-of-plane distance $D_{op}$ between the ultrasound transducer 15 and the image plane 12 by comparing the maximum detected intensity $I_{Smax}$ with a model MO describing an expected variation of in-plane maximum detected intensity $I_{SmaxInplane}$ with time of flight, at the time of flight $TOF_{Smax}$ of the ultrasound signal having the maximum detected intensity $I_{Smax}$; and
- indicating the out-of-plane distance $D_{op}$ in the reconstructed ultrasound image RUI.

As mentioned above an indication of the out-of-plane distance $D_{op}$ may be obtained through such a comparison. Comparing the maximum detected intensity $I_{Smax}$ with model MO may for instance involve determining a difference or ratio between detected intensity $I_{Smax}$ and the in-plane maximum detected intensity, $I_{SmaxInplane}$. The maximum detected intensity $I_{Smax}$ at the computed lateral position $LAP_{TOFSmax, \theta IPA}$ of the ultrasound transducer may thus be scaled to the in-plane maximum detected intensity $I_{SmaxInplane}$. By using model MO, a qualitative indication of out of plane distance $D_{op}$ may be obtained with low computational effort. Moreover, the problem of computing a potentially inaccurate position may be particularly acute at large out-of-plane distances where detected ultrasound signals from the ultrasound imaging probe are low. Thus suppressing the indicated position under the aforementioned conditions, such as the illustrated maximum detected intensity $I_{SmaxThreshold1}$ which is here exemplarily expressed as a proportion of the in-plane maximum intensity value, may be particularly beneficial in implementations in which the interventional device is routinely disposed in an out-of-plane position.

Figures 7A, 7B, 7C:
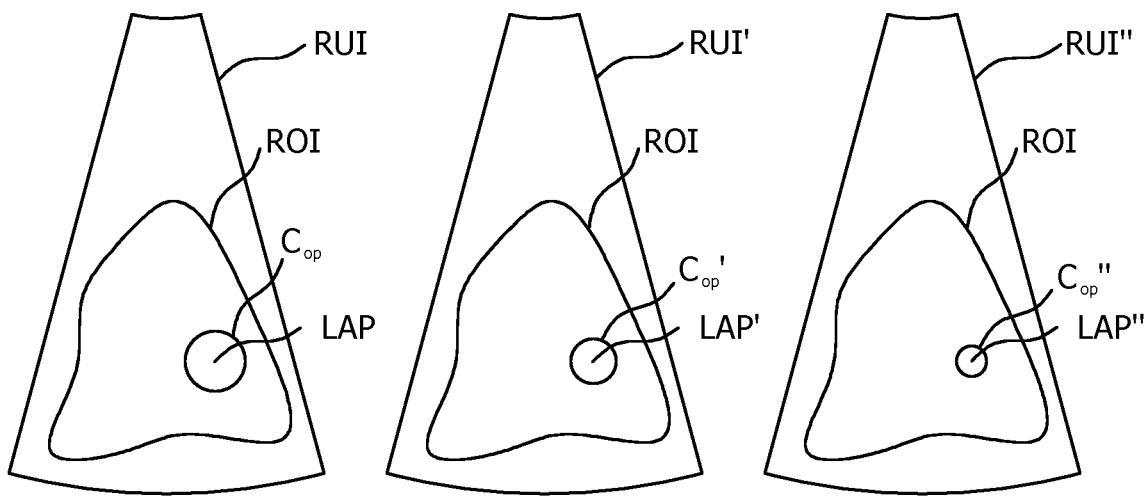
FIG. 7 illustrates a succession of reconstructed ultrasound images RUI in which an out-of-plane distance $D_{op}$ is indicated by means of a first icon $C_{op}$ at the computed lateral position $LAP_{TOFSmax, \theta IPA}$.

With reference to FIG. 7, which illustrates a succession of reconstructed ultrasound images RUI in which an out-of-plane distance $D_{op}$ is indicated by means of a first icon $C_{op}$ at the computed lateral position $LAP_{TOFSmax, \theta IP4}$ in these exemplary implementations, indicating out-of-plane distance $D_{op}$ may comprise providing a first icon $C_{op}$ at the computed lateral position $LAP_{TOFSmax, \theta IP4}$, the first icon $C_{op}$ being indicative of a circular zone with a radius corresponding to the out-of-plane distance $D_{op}$. In FIG. 7 the lateral position of interventional device 11 in reconstructed ultrasound images RUI, RUI' and RUI" remains constant respective image plane 12 and its out-of-plane distance $D_{op}$ is reduced in positions LAP' and LAP" in FIG. 7B and FIG. 7C. Consequently the corresponding radius of circles $C_{op}'$ and $C_{op}''$ is reduced. Optionally, the radius of first icon $C_{op}$ may be determined by scaling the maximum detected intensity $I_{Smax}$ to the expected in-plane maximum detected intensity $I_{SmaxInplane}$, at the time of flight $TOF_{Smax}$ of the ultrasound signal having the maximum detected intensity $I_{Smax}$.

Figure 8:
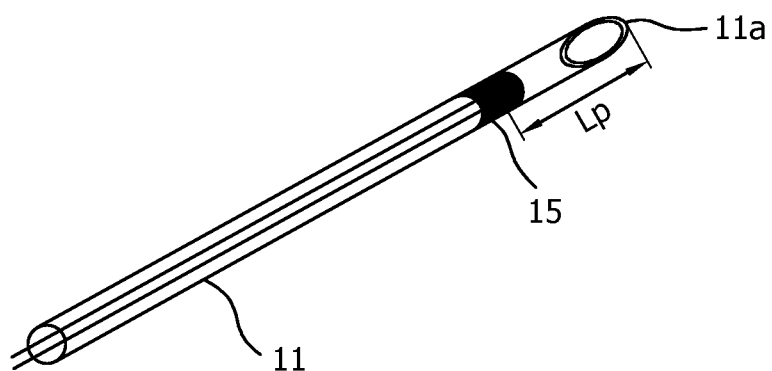
FIG. 8 illustrates an interventional device 11 that is suitable for use with system 10.

FIG. 8 illustrates an interventional device 11 that is suitable for use with system 10. Ultrasound transducer 15 may be attached at a predetermined distance $L_p$ from a feature, e.g. distal end 11a of interventional device 11. Ultrasound transducer 15 may be attached to interventional device 11 by various means including using an adhesive. Electrical conductors that carry electrical signals from ultrasound transducer 11 to position determination unit PDU are also shown, although as mentioned above it is contemplated to alternatively use a wireless link to communicate the transducer signals with position determination unit PDU.

Ultrasound transducer 15 described above with particular reference to FIG. 1, FIG. 2 and FIG. 8 may be provided by a variety of piezoelectric materials. Both hard and soft piezoelectric materials are suitable. Micromachined Electromechanical Structures, i.e. MEMS devices such as Capacitive Micromachined Ultrasound Transducers, i.e. CMUT, devices are also suitable. When the ultrasound transducer is a detector, preferably it is formed from Polyvinylidene fluoride, otherwise known as PVDF whose mechanical properties and manufacturing processes lend themselves to attachment to curved surfaces such as medical needles. Alternative materials include a PVDF co-polymer such as polyvinylidene fluoride trifluoroethylene, a PVDF ter-polymer such as P(VDF-TrFE-CTFE). Preferably the ultrasound transducer is wrapped around an axis of the interventional device in order to provide sensing around 360 degrees of rotation about the axis although this need not always be the case.

Figure 9:
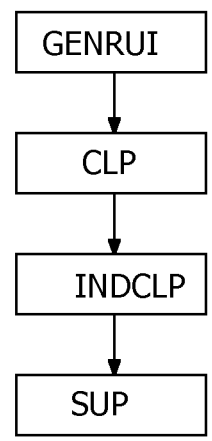
FIG. 9 illustrates various method steps of a method that may be used with system 10.

FIG. 9 illustrates various method steps of a method that may be used with system 10. With reference to FIG. 9 a method of determining a position of interventional device 11 respective image plane 12 defined by ultrasound imaging probe 13 of beamforming ultrasound imaging system 14 in which the position of interventional device 11 is determined based on ultrasound signals transmitted between ultrasound imaging probe 13 and ultrasound transducer 15 attached to interventional device 11; includes the steps of:

generating GENRUI a reconstructed ultrasound image RUI corresponding to an image plane 12 defined by the ultrasound imaging probe 13;

computing CLP a lateral position $LAP_{TOFSmax, \theta IP4}$ of the ultrasound transducer 15 respective the image plane 12 based on a time of flight $TOF_{Smax}$ of a maximum detected intensity $I_{Smax}$ ultrasound signal transmitted between the ultrasound imaging probe 13 and the ultrasound transducer 15;

indicating INDCLP the computed position $LAP_{TOFSmax, \theta IP4}$ in the reconstructed ultrasound image RUI; and suppressing SUP the indication of the computed position $LAP_{TOFSmax, \theta IP4}$ if at least one of the following conditions are met:

a rate of change of the computed position $LAP_{TOFSmax, \theta IP4}$ exceeds a first predetermined rate $R_{Max1}$;

an interference signal in the ultrasound signals exceeds a first predetermined value $Int_{Threshold1}$;

the maximum detected intensity $I_{Smax}$ is less than a first predetermined threshold $I_{SmaxThreshold1}$;

a signal to noise ratio or a signal to interference ratio of the maximum detected intensity $I_{Smax}$ is less than a first predetermined level $SNR_{ISmaxThreshold1}$.

The method may optionally include the step of:

computing an out-of-plane distance $D_{op}$ between the ultrasound transducer 15 and the image plane 12 by comparing the maximum detected intensity $I_{Smax}$ with a model MO describing an expected variation of in-plane maximum detected intensity $I_{SmaxInplane}$ with time of flight, at the time of flight $TOF_{Smax}$ of the ultrasound signal having the maximum detected intensity $I_{Smax}$.

The step of indicating INDCLP the computed position $LAP_{TOFSmax, \theta IP4}$ in the reconstructed ultrasound image RUI may optionally include:

indicating the out-of-plane distance $D_{op}$ in the reconstructed ultrasound image RUI.

It is to be noted that other implementations of the method may additionally incorporate one or more aspects described with respect to an implementation of the system.

The method steps illustrated in FIG. 9, optionally including other method steps described herein, may be stored on a computer program product as instructions that are executable by a processor. The computer program product may be provided by dedicated hardware, or hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In this respect a computer program product is also provided for use with system 10. The computer program product includes instructions which when executed on a processor of system 10 for determining a position of an interventional device 11 respective an image plane 12 defined by an ultrasound imaging probe 13 of a beamforming ultrasound imaging system 14 in which the position of the interventional device 11 is determined based on ultrasound signals transmitted between the ultrasound imaging probe 13 and an ultrasound transducer 15 attached to the interventional device 11; cause the processor to carry out the aforementioned method steps.

The disclosure is exemplified by the following enumerated Examples:

Example 1. System (10) for determining a position of an interventional device (11) respective an image plane (12) defined by an ultrasound imaging probe (13) of a beamforming ultrasound imaging system (14) in which the position of the interventional device (11) is determined based on ultrasound signals transmitted between the ultrasound imaging probe (13) and an ultrasound transducer (15) attached to the interventional device (11), the system (10) comprising:
an image reconstruction unit (IRU) configured to provide a reconstructed ultrasound image (RUI) corresponding to an image plane (12) defined by the ultrasound imaging probe (13);
a position determination unit (PDU) configured to:
compute a position ($LAP_{TOFSmax, \theta IPA}$) of the ultrasound transducer (15) respective the image plane (12) based on a time of flight ($TOF_{Smax}$) of a maximum detected intensity ($I_{Smax}$) ultrasound signal transmitted between the ultrasound imaging probe (13) and the ultrasound transducer (15); and to indicate the computed position ($LAP_{TOFSmax, \theta IPA}$) in the reconstructed ultrasound image (RUI); and
wherein position determination unit (PDU) is further configured to suppress the indication of the computed position ($LAP_{TOFSmax, \theta IPA}$) if at least one of the following conditions are met:
a rate of change of the computed position ($LAP_{TOFSmax, \theta IPA}$) exceeds a first predetermined rate ($R_{Max1}$);
an interference signal in the ultrasound signals exceeds a first predetermined value ($Int_{Threshold1}$);
the maximum detected intensity ($I_{Smax}$) is less than a first predetermined threshold ($I_{SmaxThreshold1}$);
a signal to noise ratio or a signal to interference ratio of the maximum detected intensity ($I_{Smax}$) is less than a first predetermined level ($SNR_{ISmaxThreshold1}$).

Example 2. The system (10) according to Example 1 wherein the position determination unit (PDU) is further configured to continue suppressing the indication of the computed position ($LAP_{TOFSmax, \theta IPA}$) until at least one of the following corresponding conditions have been satisfied for a predetermined period:
a rate of change of the computed position ($LAP_{TOFSmax, \theta IPA}$) is less than a second predetermined rate ($R_{Max2}$);
an interference signal in the ultrasound signals is less than a second predetermined value ($Int_{Threshold2}$);
the maximum detected intensity ($I_{Smax}$) exceeds a second predetermined threshold ($I_{SmaxThreshold2}$);
a signal to noise ratio or a signal to interference ratio of the maximum detected intensity ($I_{Smax}$) exceeds a second predetermined level ($SNR_{ISmaxThreshold2}$).

Example 3. The system (10) according to Example 2 wherein the first predetermined rate ($R_{Max1}$) is equal to the second predetermined rate ($R_{Max2}$); or wherein the first predetermined value ($Int_{Threshold1}$) is equal to the second predetermined value ($Int_{Threshold2}$); or wherein the first predetermined threshold ($I_{SmaxThreshold1}$) is equal to the second predetermined threshold ($I_{SmaxThreshold2}$); or wherein the first predetermined level ($SNR_{ISmaxThreshold1}$) is equal to the second predetermined level ($SNR_{ISmaxThreshold2}$).

Example 4. The system (10) according to any one of Examples 1-3 wherein the position determination unit (PDU) is configured to suppress the indication of the computed position ($LAP_{TOFSmax, \theta IPA}$) based on an interference signal in the ultrasound signals exceeding a first predetermined value ($Int_{Threshold1}$); and wherein the image reconstruction unit (IRU) is configured to periodically update the reconstructed ultrasound image (RUI); the ultrasound signals corresponding to each reconstructed ultrasound image (RUI) being transmitted and detected by the ultrasound imaging probe (13) during a corresponding imaging frame period ($T_f$); and wherein the position determination unit (PDU) is configured to determine the interference signal in the ultrasound signals between consecutive imaging frame periods.

Example 5. The system (10) according to any one of Examples 1-3 wherein the position determination unit (PDU) is configured to suppress the indication of the computed position ($LAP_{TOFSmax, \theta IPA}$) based on an interference signal in the ultrasound signals exceeding a first predetermined value ($Int_{Threshold1}$); and wherein the reconstructed ultrasound image (RUI) comprises a plurality of image lines ($L_{1 \ldots n}$), each line corresponding to a depth dimension in the ultrasound image; and wherein the ultrasound signals corresponding to each line of the reconstructed ultrasound image (RUI) are transmitted and detected by the ultrasound imaging probe (13) during a corresponding image line period ($T_1$); and wherein the position determination unit (PDU) is configured to determine the interference signal in the ultrasound signals between consecutive image line periods.

Example 6. The system (10) according to any previous Example wherein indicating the computed position ($LAP_{TOFSmax, \theta IPA}$) in the reconstructed ultrasound image (RUI) includes:
computing an out-of-plane distance ($D_{op}$) between the ultrasound transducer (15) and the image plane (12) by comparing the maximum detected intensity ($I_{Smax}$) with a model (MO) describing an expected variation of in-plane maximum detected intensity ($I_{SmaxInplane}$) with time of flight, at the time of flight ($TOF_{Smax}$) of the ultrasound signal having the maximum detected intensity ($I_{Smax}$); and
indicating the out-of-plane distance ($D_{op}$) in the reconstructed ultrasound image (RUI).

17

Example 7. The system (10) according to Example 6 wherein indicating the out-of-plane distance ($D_{op}$) comprises providing a first icon ($C_{op}$) at the computed lateral position ($LAP_{TOFSmax, \theta IPA}$), the first icon ($C_{op}$) being indicative of a circular zone with a radius corresponding to the out-of-plane distance ($D_{op}$).

Example 8. The system (10) according to Example 7 wherein the radius is determined based on scaling the maximum detected intensity ($I_{Smax}$) to the expected in-plane maximum detected intensity ($I_{SmaxInplane}$), at the time of flight ($TOF_{Smax}$) of the ultrasound signal having the maximum detected intensity ($I_{Smax}$).

Example 9. The system (10) according to any previous Example further comprising an interventional device (11) having an ultrasound transducer (15) attached thereto.

Example 10. Method of determining a position of an interventional device (11) respective an image plane (12) defined by an ultrasound imaging probe (13) of a beamforming ultrasound imaging system (14) in which the position of the interventional device (11) is determined based on ultrasound signals transmitted between the ultrasound imaging probe (13) and an ultrasound transducer (15) attached to the interventional device (11); the method comprising the steps of:

- generating (GENRUI) a reconstructed ultrasound image (RUI) corresponding to an image plane (12) defined by the ultrasound imaging probe (13);
- computing (CLP) a lateral position ($LAP_{TOFSmax, \theta IPA}$) of the ultrasound transducer (15) respective the image plane (12) based on a time of flight ($TOF_{Smax}$) of a maximum detected intensity ($I_{Smax}$) ultrasound signal transmitted between the ultrasound imaging probe (13) and the ultrasound transducer (15);
- indicating (INDCLP) the computed position ($LAP_{TOFSmax, \theta IPA}$) in the reconstructed ultrasound image (RUI); and
- suppressing (SUP) the indication of the computed position ($LAP_{TOFSmax, \theta IPA}$) if at least one of the following conditions are met:
  - a rate of change of the computed position ($LAP_{TOFSmax, \theta IPA}$) exceeds a first predetermined rate ($R_{Max1}$);
  - an interference signal in the ultrasound signals exceeds a first predetermined value ($Int_{Threshold1}$);
  - the maximum detected intensity ($I_{Smax}$) is less than a first predetermined threshold ($I_{SmaxThreshold1}$);
  - a signal to noise ratio or a signal to interference ratio of the maximum detected intensity ($I_{Smax}$) is less than a first predetermined level ($SNR_{ISmaxThreshold1}$).

Example 11. The method according to Example 10 further comprising:

- computing an out-of-plane distance ($D_{op}$) between the ultrasound transducer (15) and the image plane (12) by comparing the maximum detected intensity ($I_{Smax}$) with a model (MO) describing an expected variation of in-plane maximum detected intensity ($I_{SmaxInplane}$) with time of flight, at the time of flight ($TOF_{Smax}$) of the ultrasound signal having the maximum detected intensity ($I_{Smax}$); and
- wherein the step of indicating (INDCLP) the computed position ($LAP_{TOFSmax, \theta IPA}$) in the reconstructed ultrasound image (RUI) further comprises:
  - indicating the out-of-plane distance ($D_{op}$) in the reconstructed ultrasound image (RUI).

Example 12. Computer program product comprising instructions which when executed on a processor of a system (10) for determining a position of an interventional device (11) respective an image plane (12) defined by an ultrasound imaging probe (13) of a beamforming ultrasound imaging system (14) in which the position of the interventional device (11) is determined based on ultrasound signals transmitted between the ultrasound imaging probe (13) and an ultrasound transducer (15) attached to the interventional device (11); cause the processor to carry out the method steps of Example 11.

In summary a system has been described for determining a position of an interventional device respective an image plane defined by an ultrasound imaging probe of a beamforming ultrasound imaging system in which the position of the interventional device is determined based on ultrasound signals transmitted between the ultrasound imaging probe and an ultrasound transducer attached to the interventional device. The system includes an image reconstruction unit and a position determination unit. The image reconstruction unit provides a reconstructed ultrasound image corresponding to an image plane defined by the ultrasound imaging probe. The position determination unit computes a position of the ultrasound transducer respective the image plane based on a time of flight of a maximum detected intensity ultrasound signal transmitted between the ultrasound imaging probe and the ultrasound transducer. The position determination unit also indicates the computed position in the reconstructed ultrasound image. Moreover, the position determination unit suppresses the indication of the computed position if at least one of the following conditions are met:

- a rate of change of the computed position exceeds a first predetermined rate;
- an interference signal in the ultrasound signals exceeds a first predetermined value;
- the maximum detected intensity is less than a first predetermined threshold;
- a signal to noise ratio or a signal to interference ratio of the maximum detected intensity is less than a first predetermined level.

Whilst the invention has been illustrated and described in detail in the drawings and foregoing description in relation to a medical needle, such illustrations and descriptions are to be considered illustrative or exemplary and not restrictive. Any reference signs in the claims should not be construed as limiting the scope of the invention. Moreover it is to be understood that the various examples, implementations and embodiments illustrated herein may be combined in order to provide various systems and methods for determining a position of an interventional device respective an image plane of a beamforming ultrasound imaging system.

As used herein, the term "or" should be interpreted as a disjunctive "or". Further, the term "or" and the term "and" when prefaced by the term "at least one of" or the term by "one or more of" should be interpreted as a disjunctive list such that, for example, a list of "at least one of A or B" or a list of "one or more of A or B" or a list of "A or B" should be interpreted to include either A or B, one of A and one of B, a combination of one or more of each of A and B; both A and B; or combinations of one or more of A and B, and such other combinations as relevant to the recited list or terms consistent with the recited description in the specification.

The invention claimed is:

1. A system for determining a position of an interventional device relative to an image plane defined by an ultrasound imaging probe of a beamforming ultrasound imaging system, the system comprising:

an image reconstruction processor configured to provide a reconstructed ultrasound image corresponding to the image plane defined by the ultrasound imaging probe; and
a position determination processor configured to:
  detect a maximum intensity ultrasound signal from among ultrasound signals transmitted between the ultrasound imaging probe and an ultrasound transducer attached to the interventional device,
  compute a position of the ultrasound transducer relative to the image plane based on a time of flight of the maximum detected intensity ultrasound signal,
  indicate the computed position of the ultrasound transducer in the reconstructed ultrasound image, and
  suppress entirely indication of the position of the ultrasound transducer in the reconstructed ultrasound image if a rate of change of the computed position exceeds a first predetermined rate.

2. The system according to claim 1, wherein the position determination processor is further configured to continue suppressing the indication of the position of the ultrasound transducer until the rate of change of the computed position is less than a second predetermined rate.

3. The system according to claim 2, wherein the first predetermined rate is equal to the second predetermined rate.

4. The system according to claim 1, wherein:
the image reconstruction processor is further configured to periodically update the reconstructed ultrasound image;
wherein the ultrasound signals corresponding to each reconstructed ultrasound image are transmitted and detected by the ultrasound imaging probe during a corresponding imaging frame period.

5. The system according to claim 1,
wherein the reconstructed ultrasound image comprises a plurality of image lines, each image line corresponding to a depth dimension in the reconstructed ultrasound image; and
wherein ultrasound signals corresponding to each line of the reconstructed ultrasound image are transmitted and detected by the ultrasound imaging probe during a corresponding image line period.

6. The system according to claim 1, wherein indicating the computed position in the reconstructed ultrasound image includes:
computing an out-of-plane distance between the ultrasound transducer and the image plane by comparing the intensity of the maximum detected intensity ultrasound signal, at the time of flight of the maximum detected intensity ultrasound signal, with a model describing an expected variation of in-plane maximum detected intensity with time of flight; and
indicating the out-of-plane distance in the reconstructed ultrasound image.

7. The system according to claim 6, wherein indicating the out-of-plane distance comprises providing a first icon at the computed position, the first icon being indicative of a circular zone with a radius corresponding to the out-of-plane distance.

8. The system according to claim 7, wherein the radius is determined based on scaling the intensity of the maximum detected intensity ultrasound signal to the expected in-plane maximum detected intensity.

9. The system according to claim 1, further comprising the interventional device with the ultrasound transducer attached thereto.

10. A method of determining a position of an interventional device relative to an image plane defined by an ultrasound imaging probe of a beamforming ultrasound imaging system, the method comprising:
generating a reconstructed ultrasound image corresponding to the image plane defined by the ultrasound imaging probe;
detecting a maximum intensity ultrasound signal from among ultrasound signals transmitted between the ultrasound imaging probe and an ultrasound transducer attached to the interventional device;
computing a position of the ultrasound transducer relative to the image plane based on a time of flight of the maximum detected intensity ultrasound signal;
indicating the computed position of the ultrasound transducer in the reconstructed ultrasound image; and
suppressing entirely indication of the position of the ultrasound transducer in the reconstructed ultrasound image if a rate of change of the computed position exceeds a first predetermined rate.

11. The method according to claim 10, further comprising:
computing an out-of-plane distance between the ultrasound transducer and the image plane by comparing intensity of the maximum detected intensity ultrasound signal, at the time of flight of the maximum detected intensity ultrasound signal, with a model describing an expected variation of in-plane maximum detected intensity with time of flight; and
indicating the out-of-plane distance in the reconstructed ultrasound image.

12. The method according to claim 11, wherein indicating the out-of-plane distance comprises providing a first icon at the computed position of the ultrasound transducer, the first icon being indicative of a circular zone with a radius corresponding to the out-of-plane distance.

13. The method according to claim 12, wherein the radius is determined based on scaling the intensity of the maximum detected intensity ultrasound signal to the expected in-plane maximum detected intensity.

14. The method according to claim 10, further comprising:
continuing to suppress the indication of the position of the ultrasound transducer until the rate of change of the computed position is less than a second predetermined rate.

15. A non-transitory computer readable medium having stored thereon instructions for determining a position of an interventional device relative to an image plane defined by an ultrasound imaging probe of a beamforming ultrasound imaging system, the instructions, when executed on a processor, cause the processor to:
generate a reconstructed ultrasound image corresponding to the image plane defined by the ultrasound imaging probe;
detect a maximum intensity ultrasound signal from among ultrasound signals transmitted between the ultrasound imaging probe and an ultrasound transducer attached to the interventional device;
compute a position of the ultrasound transducer relative to the image plane based on a time of flight of the maximum detected intensity ultrasound signal;
indicate the computed position in the reconstructed ultrasound image; and suppress entirely indication of the position of the ultrasound transducer in the reconstructed ultrasound image if a rate of change of the computed position exceeds a first predetermined rate.

16. The non-transitory computer readable medium according to claim 15, wherein the instructions, when executed by the processor, further cause the processor to:
compute an out-of-plane distance between the ultrasound transducer and the image plane by comparing intensity of the maximum detected intensity ultrasound signal, at the time of flight of the maximum detected intensity ultrasound signal, with a model describing an expected variation of in-plane maximum detected intensity with time of flight; and
indicate the out-of-plane distance in the reconstructed ultrasound image.

17. The non-transitory computer readable medium according to claim 16, wherein indicating the out-of-plane distance comprises providing a first icon at the computed position of the ultrasound transducer, the first icon being indicative of a circular zone with a radius corresponding to the out-of-plane distance.

18. The non-transitory computer readable medium according to claim 17, wherein the radius is determined based on scaling the intensity of the maximum detected intensity ultrasound signal to the expected in-plane maximum detected intensity.

19. The non-transitory computer readable medium according to claim 15, wherein the instructions, when executed by the processor, further cause the processor to:
continue to suppress the indication of the position of the ultrasound transducer until the rate of change of the computed position is less than a second predetermined rate.

20. The non-transitory computer readable medium according to claim 19, wherein the first predetermined rate is equal to the second predetermined rate.

* * * * *